(12) United States Patent
Dollimer et al.

(10) Patent No.: US 8,805,538 B2
(45) Date of Patent: Aug. 12, 2014

(54) MEDICAL ELECTRICAL LEAD

(71) Applicant: Medtronic, Inc., Minneapolis, MN (US)

(72) Inventors: Michael R. Dollimer, Rosemount, MN (US); Gregory A. Boser, Richfield, MN (US); Mark D. Breyen, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/803,446

(22) Filed: Mar. 14, 2013

(65) Prior Publication Data
US 2013/0197616 A1 Aug. 1, 2013

Related U.S. Application Data

(63) Continuation of application No. 13/305,940, filed on Nov. 29, 2011, now abandoned.

(51) Int. Cl.
*A61N 1/05* (2006.01)
*A61N 1/04* (2006.01)

(52) U.S. Cl.
CPC .. *A61N 1/048* (2013.01); *A61N 1/05* (2013.01)
USPC .......................................................... 607/116

(58) Field of Classification Search
CPC ....... A61N 1/05; A61N 1/0551; A61N 1/048; A61N 1/36

USPC .................................................. 607/115–122
See application file for complete search history.

(56) References Cited

U.S. PATENT DOCUMENTS

| 5,423,881 | A | * | 6/1995 | Breyen et al. ................. 607/122 |
| 5,824,077 | A | | 10/1998 | Mayer |
| 5,935,159 | A | | 8/1999 | Cross, Jr. et al. |
| 7,787,961 | B1 | * | 8/2010 | Safarevich et al. .......... 607/116 |
| 2005/0113898 | A1 | | 5/2005 | Honeck et al. |
| 2005/0240252 | A1 | | 10/2005 | Boser et al. |
| 2005/0256557 | A1 | | 11/2005 | Wessman et al. |

FOREIGN PATENT DOCUMENTS

WO 2011/005716 A2 1/2011

OTHER PUBLICATIONS (PCT/US2011/062978) PCT Notification of Transmittal of the International Search Report and the Written Opinion of the International Searching Authority, Mailed Mar. 14, 2012, 10 pages.

* cited by examiner

*Primary Examiner* — Rex R Holmes
(74) *Attorney, Agent, or Firm* — Evans M. Mburu

(57) ABSTRACT

An improved medical electrical lead is disclosed herein. The lead may include a longitudinally extending body having a distal end, a proximal end, a conductive element extending between the distal and proximal ends, and an electrode coupled to the conductive element utilizing a reflow process. The conductive element and electrode may comprise materials that are incompatible.

14 Claims, 12 Drawing Sheets

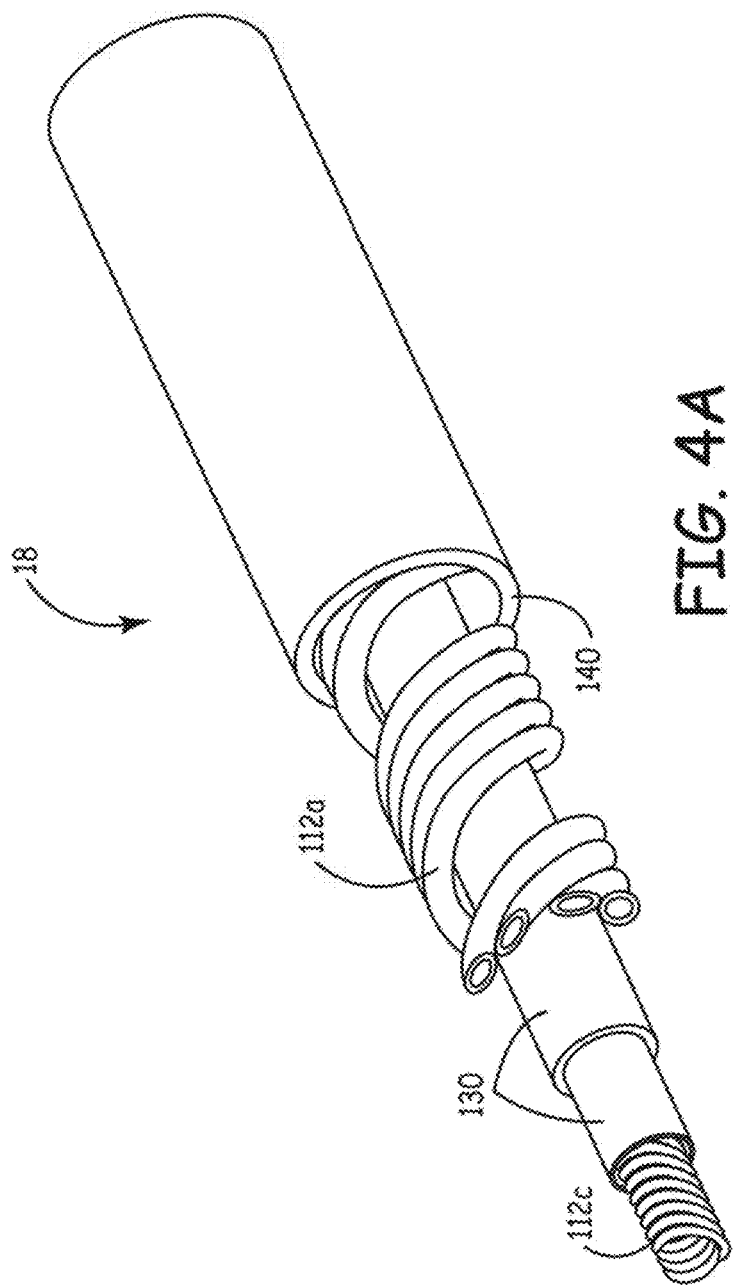

MEDICAL ELECTRICAL LEAD

TECHNICAL FIELD

The present application relates to implantable medical devices and, more particularly, leads for electrical stimulators.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof. The electrical therapy produced by an IMD may include, for example, pacing pulses, cardioverting pulses, and/or defibrillator pulses to reverse arrhythmias (e.g. tachycardias and bradycardias) or to stimulate the contraction of cardiac tissue (e.g. cardiac pacing) to return the heart to its normal sinus rhythm.

In general, the IMDs include a battery and electronic circuitry, such as a pulse generator and/or a processor module, that are hermetically sealed within a housing (generally referred to as the "can"). An implantable lead interconnects the IMD and the heart. Typically, a medical electrical lead includes a flexible elongated body with one or more insulated elongated conductors. Each conductor electrically couples a sensing and/or a stimulation electrode of the lead to the electronic circuitry through a connector module. Electrical signals are transmitted between the electrodes and the pulse generator. For an IMD, functional implant life time is, in part, determined by the energy delivered per pulse. The IMD will have a longer life if the energy delivered per pulse can be maintained at a minimum. Designs of the lead and of the electrodes which are used with the lead are influenced by the electrical signal required for pacing stimulation. Physiologically, the IMD should be capable of generating a signal with a sufficient magnitude to depolarize the excitable cells of the myocardium to initiate contraction. The electrode shape, size, surface area, material and impedance combine to determine the energy required of the IMD.

In the context of medical electrical leads, a tubular electrode may typically be mounted around the exterior of an insulative lead body and coupled to an elongated conductive coil within the lead body. Different combinations of materials have been proposed for the electrode and conductive coils in the lead construction. However, the inventors of the present disclosure have found that conventional techniques utilized in joining different combinations of materials present challenges in the construction of leads having different combinations of materials. For example, the techniques utilized in joining some of these materials have been found to result in formation of intermettalics when the materials used have incompatible compounds. A property of intermettalics is brittleness which results in cracks and uneven surfaces thereby compromising the electrical conductivity and mechanical integrity of the lead.

Some proposals to overcome the above and other disadvantages have included cladding the conductive coil with a suitable material prior to coupling with another component. For example, the conductive coil may be cladded with the suitable material and the cladded portion of the conductor is then welded to the other component.

Therefore, there remains a need for an improved method of constructing an implantable lead having incompatible materials that are coupled directly, while maintaining the desired electrical conductivity and mechanical integrity.

BRIEF SUMMARY OF THE DISCLOSURE

An implantable medical lead is disclosed. It is generally desirable to provide medical leads that have intact mechanical and electrical connectivity. Accordingly, in contrast to the conventional coupling techniques, the present disclosure provides exemplary construction and coupling techniques for leads having various combinations of materials.

In one embodiment, the lead may include a longitudinally extending body having a distal end, a proximal end, a conductive element, such as a cable, extending between the distal and proximal ends, and an outer jacket about the conductive element. At least one electrode is connected to the conductive element. In some embodiments, the connection between the conductive element and the electrode is achieved by reflowing a portion of the conductive element onto the electrode.

In some embodiments, the electrode is constructed of a first material and the conductive element is constructed of a second material. The first and second materials may be selected from materials consisting essentially of at least one of the following: tantalum, platinum, gold, iridium, rhenium, tungsten, ruthenium, depleted uranium, cobalt, chromium, titanium, aluminum, vanadium, chromium, nickel, molybdenum, iron, copper, silver, gold, stainless steel, magnesium-nickel, palladium and alloys thereof.

The present disclosure also relates to methods of manufacturing medical electrical leads. In one embodiment, the method includes: providing a longitudinally extending conductive element and providing an outer jacket about the conductive element. In an embodiment, a tubular electrode is positioned over and attached to the outer jacket. The tubular electrode is coupled to the conductive element. In some embodiments, the coupling is achieved by heating the conductive element to a molten state and manipulating it to flow over the electrode.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

Embodiments of the present disclosure will hereinafter be described in conjunction with the following drawings wherein like reference numerals denote like elements throughout.

FIGS. 4A and 4B depict two exemplary embodiments of lead body construction that may be used in connection with the medical electrical leads of the present disclosure.

DETAILED DESCRIPTION OF THE DISCLOSURE

Figure 1:
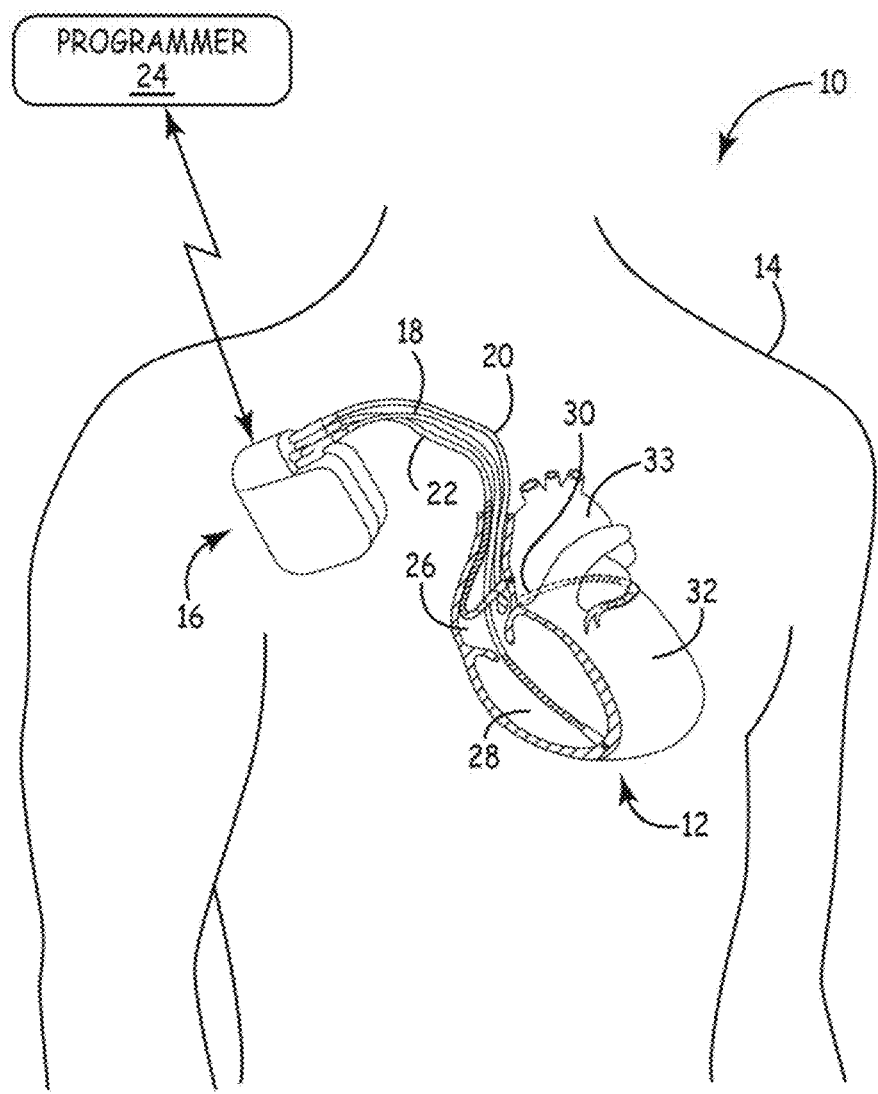
FIG. 1 is a conceptual diagram illustrating an example therapy system 10 that may be used to provide therapy to a heart of a patient.

In the following detailed description, reference is made to the accompanying figures of the drawing which form a part hereof, and in which are shown, by way of illustration, specific embodiments. It is to be understood that other embodiments may be utilized and structural changes may be made without departing from the scope of the present disclosure.

FIG. 1 is a conceptual diagram illustrating an example therapy system 10 that may be used to provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
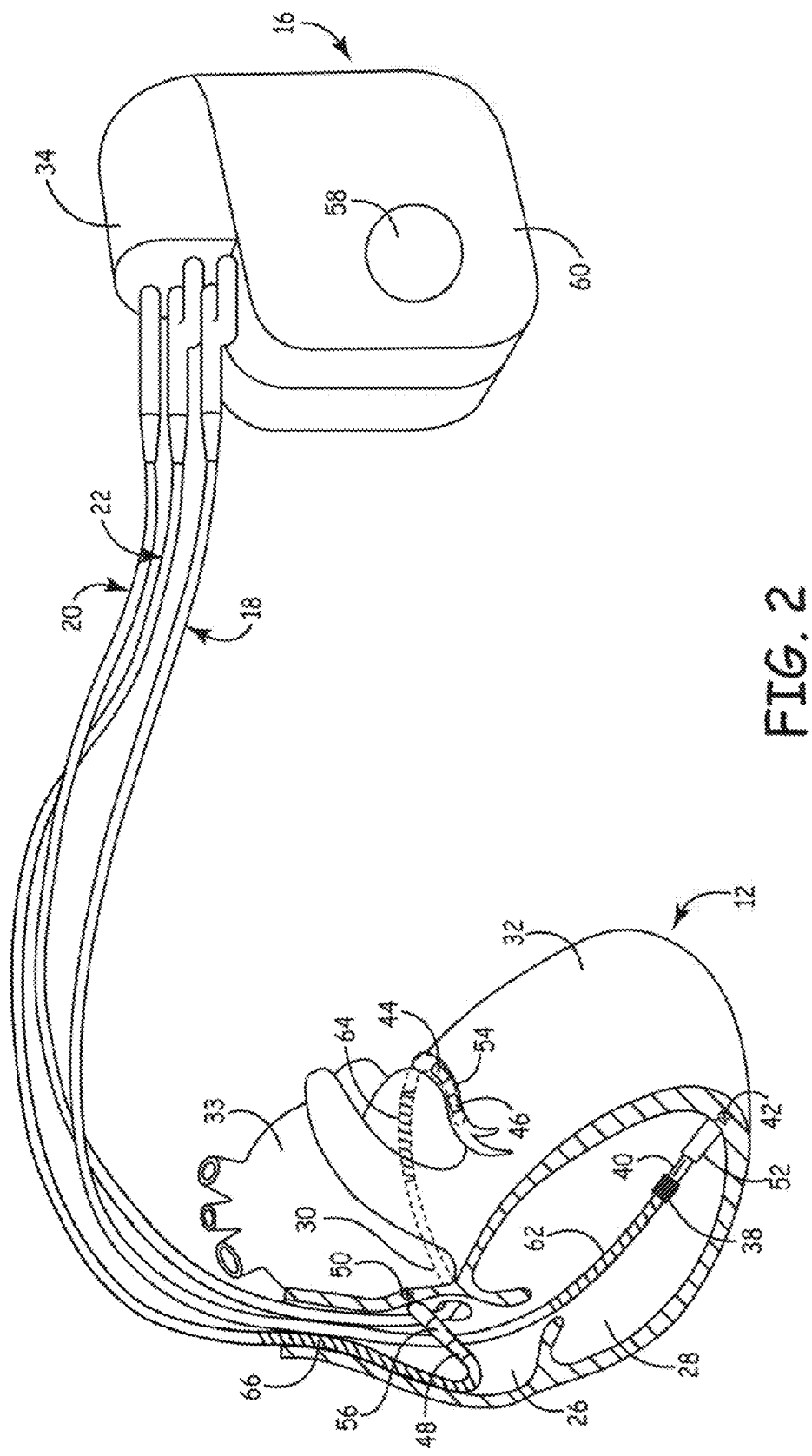
FIG. 2 is a conceptual diagram illustrating an implantable medical device and leads of therapy system 10 in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Among the electrodes, some of the electrodes may be provided in the form of coiled electrodes that form a helix, while other electrodes may be provided in different forms. Further, some of the electrodes may be provided in the form of tubular electrode sub-assemblies that can be pre-fabricated and positioned over the body of leads 18, 20, 22, where they are attached and where electrical connections with conductive elements within the leads 18, 20, 22 can be made. For example, electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As is known in the art, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. Other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
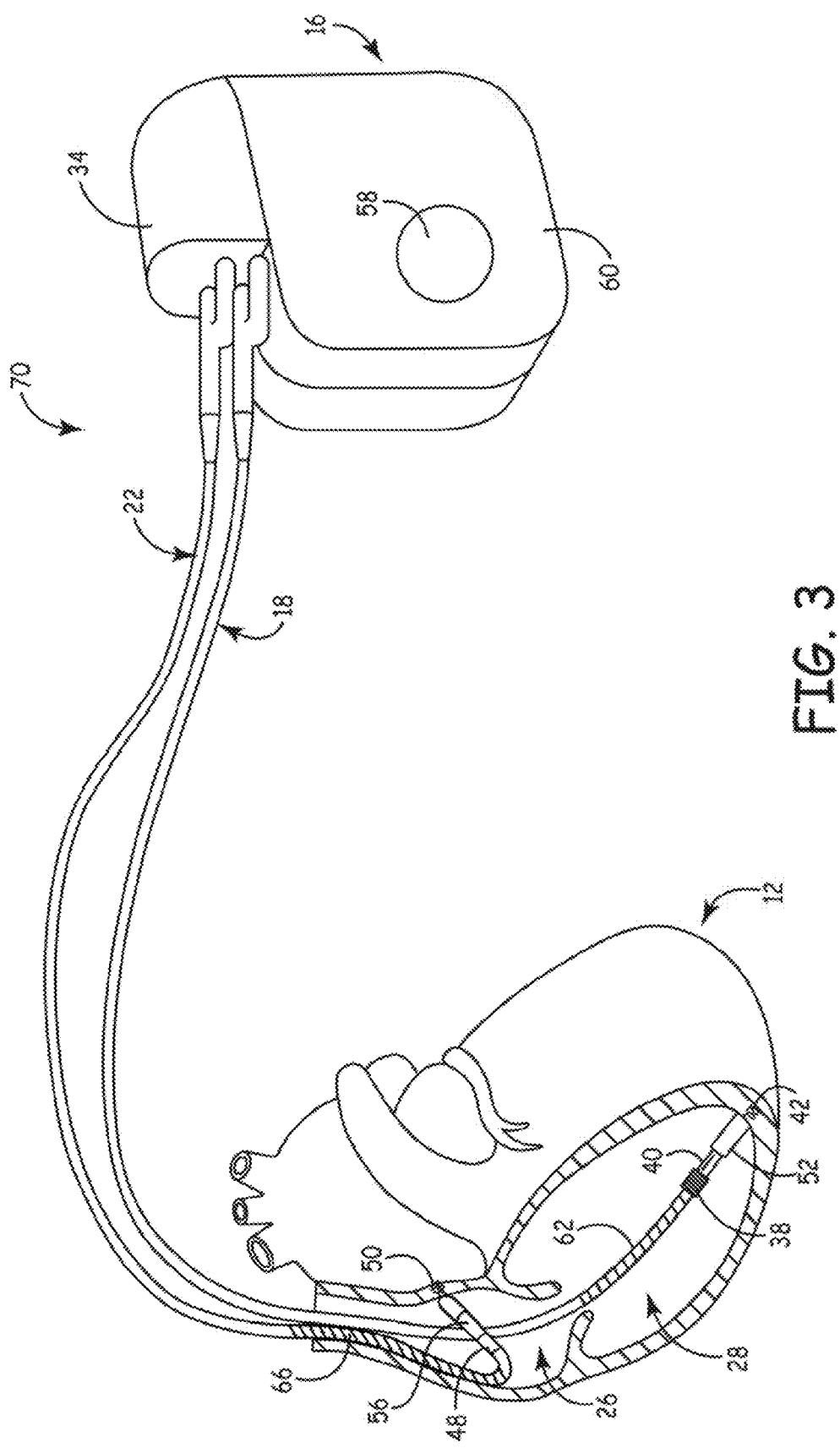
FIG. 3 is a conceptual diagram illustrating another exemplary therapy system.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4B:
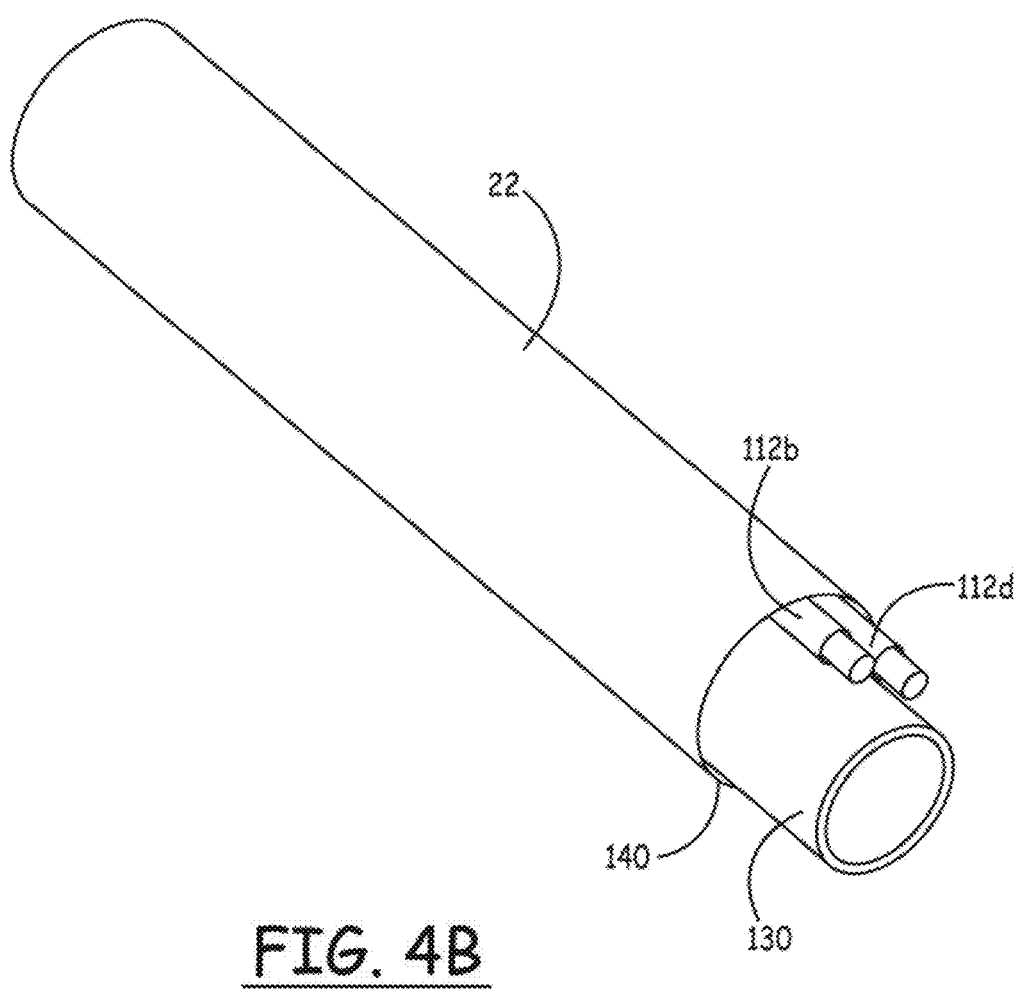

FIGS. 4A and 4B depict two exemplary embodiments of lead body construction that may be used in connection with the medical electrical leads 18 and 22 of the present disclosure. The illustrative embodiments of FIGS. 4A and 4B depict portions of leads 18 and 22, respectively, before electrodes are coupled thereto. It should, however, be noted that the construction of the lead bodies discussed with respect to leads 18 and 22 may be employed interchangeably or together on any of the exemplary leads 18, 20, and 22. Referring to FIG. 4A, one example of a lead body is depicted (with respect to lead 18) having conductive elements 112a, 112c that are provided in a wrapped configuration. The depicted lead 18 also comprises one or more internal jackets 130 with an outer jacket 140 that surrounds the one or more internal jackets 130. According to embodiments of the present disclosure at least one conductive fitting (shown in FIG. 7) is coupled to each of conductive elements 112a and 112c. That coupling may be made by a variety of techniques, with at least some potentially suitable connection techniques being described in U.S. Patent Application Publication Nos. U.S. 2005/0240252 (Boser et al.); U.S. 2005/0113898 (Honeck et al.), incorporated herein by reference in their entirety.

FIG. 4B depicts another lead body (of exemplary lead 22) that includes conductive elements 112b and 112d that extend linearly along the length of the lead body. The conductive elements 112b and 112d may be located between an inner jacket 130 and an outer jacket 140. In some embodiments, both wrapped (112a, 112c) and linear (112b, 112d) conductive elements may be provided in the same lead body. In another embodiment (not shown), an exemplary lead body that may be used is a multi-lumen tubular structure (symmetric or asymmetric), which is known to those skilled in the art.

An example of an appropriate material for the conductive elements 112a, 112b, 112c and 112d employed by embodiments of the present disclosure is an MP35N alloy with one or more of the conductive elements further including a low resistance core, for example silver. Other examples of appropriate material include tantalum, platinum, gold, iridium, rhenium, tungsten, ruthenium, depleted uranium, cobalt, chromium, titanium, aluminum, vanadium, chromium, nickel, molybdenum, iron, copper, silver, gold, stainless steel, magnesium-nickel, palladium. It should be noted that the listing of materials is not intended to be limiting and other exemplary materials may comprise combinations of the aforementioned materials and/or alloys thereof. According to some embodiments of the present disclosure, internal jacket 130 and external jacket 140 are formed from an insulative material, examples of which include fluoropolymers, silicones, and polyurethanes. Specific examples of an appropriate material for internal jacket 130 and external jacket 140 are Ethylene tetrafluoroethylene (ETFE) and PolyEtherEtherKetone (PEEK). It should be noted that according to some embodiments, when the conductive elements 112a, 112b, 112c and 112d are positioned along internal jacket 130, they can be embedded in an outer surface of the internal jacket 130.

Figure 5:
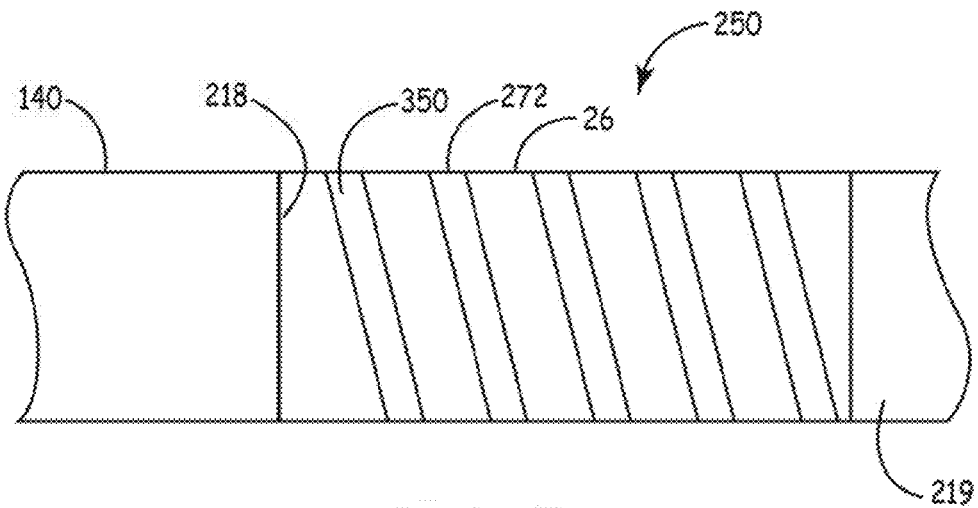
FIGS. 5 and 6 show an exemplary embodiment of a lead sub-assembly of a lead constructed in accordance with embodiments of the present disclosure.
Figure 6:
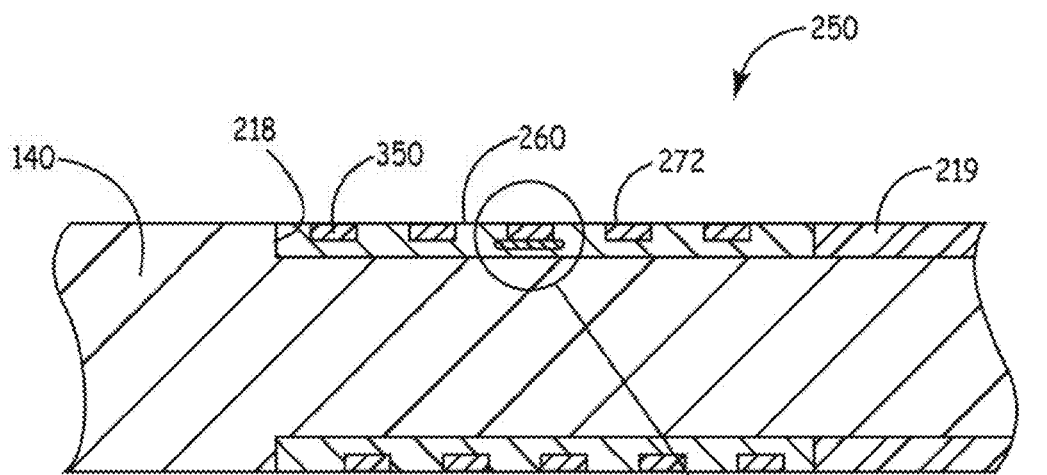
Figure 7:
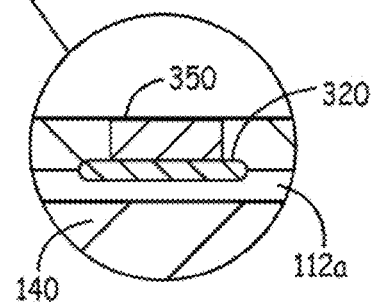
FIG. 7 is a cutaway perspective view of the lead sub-assembly as shown in FIG. 6.

Turning to FIGS. 5 and 6, an exemplary embodiment of a lead sub-assembly 250 of any of leads 18, 20 and 22 is depicted, where an electrode sub-assembly 350 of any of electrodes 40, 44 and 48 is positioned over external jacket 140. The electrode 350 is preferably embedded in an outer surface 260 of external jacket 140 to a depth that is sufficient to mechanically and electrically couple the electrode 350 to the appropriate conductive element 112a, 112c directly or through a conductive fitting (FIG. 7). At least a portion of the outer surface 272 of the electrode 350 is exposed proximate to the outer surface 260 such that the electrode 350 can be placed in electrical communication with tissue and/or fluids surrounding the electrode sub-assembly 350.

Another optional feature depicted in FIGS. 5 and 6 is that the lead body of lead sub-assembly 250 may be constructed with a variable diameter such that the area in which the electrode sub-assembly 350 is positioned has a reduced size as compared to other portions of the lead body. For example, the lead sub-assembly 250 may include a shoulder 218 as seen in FIG. 6 where the diameter of the lead body decreases. The diameter of the lead body may be increased on the opposite end of the electrode sub-assembly 350 by optionally including a sleeve 219 or other structure to increase the size of the lead. Such a construction can be used to provide an isodiametric lead, although other constructions could also be used to compensate for the thickness of the electrode sub-assembly 350.

The electrode 350 may, in some embodiments, be formed in the shape of a coil with one or more wraps or coils and using a wire element having a rectangular cross-section as depicted in FIG. 6, although coiled electrodes in other embodiments may be formed using wire elements having any selected shape (e.g., round, oval, elliptical, etc.)

FIG. 7 is a cutaway perspective view of the lead sub-assembly 250 as shown in FIG. 6. According to the embodiment, conductive element 112a is coupled to electrode 350 via a conductive fitting 320; according to this embodiment, conductive fitting 320 is coupled to conductive element 112a prior to positioning the conductive element in the lead body. In alternate embodiments, fitting 320 may be coupled to conductive element 112a after conductive element 112a has been positioned in internal jacket 130. A portion of the aforementioned internal jacket 130 surrounding conductive element 112a is removed to expose conductive element 112a in order to couple fitting 320 to conductive element 112a. Means for removing the insulation in proximity to the fitting are well known to those skilled in the art and include but are not limited to, mechanical and laser stripping. It should be noted that although FIG. 7 shows the insulative portion removed for coupling with fitting 320, other types of fittings having internal features to penetrate internal jacket 130 may be employed so that internal jacket 130 need not be removed for coupling. Furthermore, according to other embodiments of the present disclosure, electrode 350 is coupled directly to conductive element 112a.

Figure 8A:
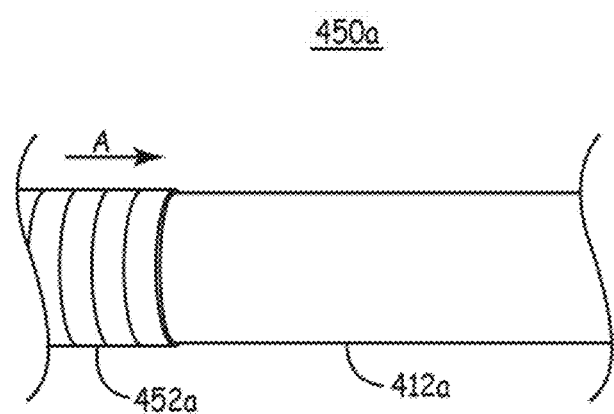
FIGS. 8A-8B are plan views each illustrating a step of an assembly of a portion of a lead sub-assembly according to embodiments of the present disclosure.
Figure 8B:
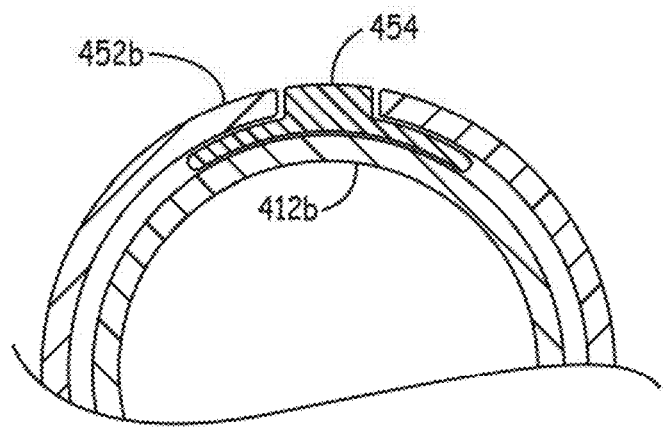

FIGS. 8A-8B are plan views, each illustrating a step of an assembly of lead sub-assembly portions according to embodiments of the present disclosure. For ease of discussion, the illustration of the assembly of lead sub-assemblies 450a, 450b has been simplified to include the components that are pertinent to the discussion and those skilled in the art will recognize that several other components can be included.

Accordingly, FIG. 8A depicts lead sub-assembly 450a having an uninsulated portion of a conductive element 412a. An electrode 452a is positioned on the conductive element 412a at a desired mounting location and may be pressed against lead subassembly 450a per arrow A. The conductive element 412a is "reflown" over the electrode 452a to achieve mechanical coupling. As used herein, a reflow process refers to any known technique that permits the heating of the conductive element 412a to a melting point such that the resulting molten substance can be manipulated as desired during construction. Exemplary techniques utilizing the reflow process include laser welding where the laser beam is projected at a pre-selected location on the conductive element 412a as will be discussed further in conjunction with FIG. 9. The laser beam has a frequency in the range of about 5-15 Hz, with an energy level between 0.5-3 J and is applied for a duration in the range of 0.5-3.0 ms.

FIG. 8B is a section view of lead sub-assembly 450b according to an alternate embodiment of the present disclosure. According to this embodiment, a conductive fitting 454 is coupled to a conductive element 412b. The material used for construction of the conductive fitting 454 is preferably identical to, but may also be selected from a variety of materials that are compatible with, the material used to construct the conductive element 412b. Often, compounds having dissimilar chemical properties will exhibit cracking and other imperfections when fused together through conventional bonding techniques; in other words, they are incompatible. Thus, as used in this disclosure, compatibility refers to the ability of two compounds to fuse together without compromising the structural integrity of the bonding junction. With continued reference to FIG. 8B, an electrode 452b is positioned at a desired mounting location on the conductive fitting 454. A portion of the conductive fitting 454 is reflown to achieve the coupling to the electrode 452b. In alternative embodiments, the material of conductive fitting 454 may be selected to be compatible with the material of an electrode 452b. In such embodiments, the reflow process will be utilized to couple the conductive fitting 454 to the conductive element 412b.

Figure 9:
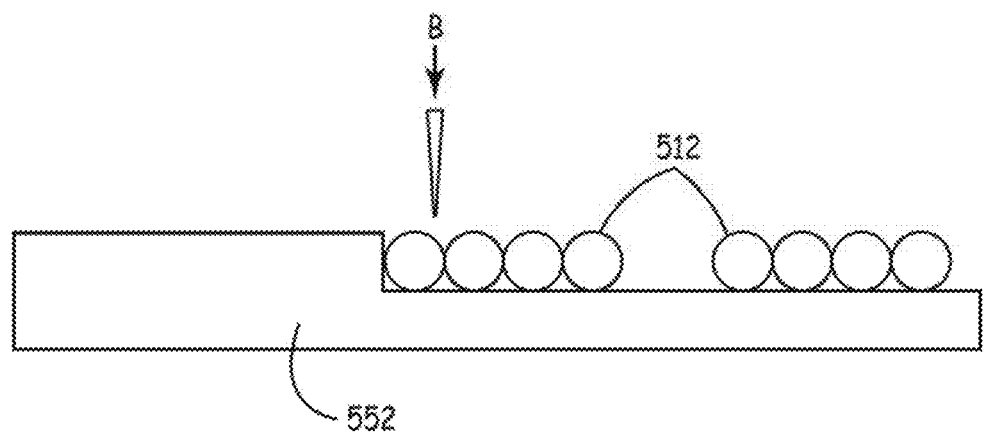
FIG. 9 illustrates a longitudinal section view of a lead assembly according to an embodiment of the present disclosure.

FIG. 9 illustrates a longitudinal cross-sectional view of a lead assembly according to an embodiment of the present disclosure. The illustration of FIG. 9 depicts a conductive element 512 that is placed adjacent to electrode 552 in anticipation of the coupling process in accordance with one embodiment of the present disclosure. Generally, the coupling involves a reflow process, where a first material having a lower melting point relative to the melting point of a second material is heated to a melting point and the molten substance is manipulated to flow over and form a covering layer on a portion of the second material. Thus, although the temperature of the second material will rise, the material remains in a solid state because of its relatively higher melting point. In the exemplary embodiment, a laser beam is directed at the conductive element 512, generally in the direction of arrow B, to cause it to heat up and reach a molten state. The resulting molten substance of conductive element 512 may then be manipulated onto the electrode 552 through physical relocation or by positioning the assembly to enable gravitational force to influence the molten substance to flow over the electrode 552. It should be noted that illustration and description of various components typically utilized for construction of a medical lead have been omitted for ease of discussion. Further details on the omitted components and description are known to those of skill in the art and exemplary descriptions can be found in U.S. Pat. No. 5,935,159 (Cross, Jr., et al.), incorporated herein by reference in its entirety.

Figure 10:
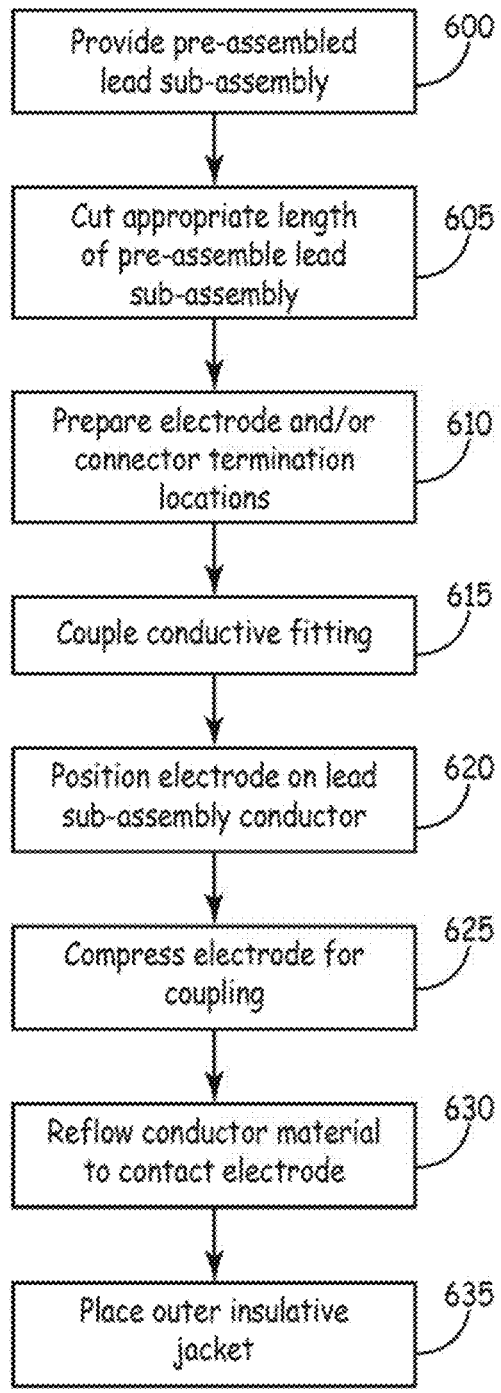
FIG. 10 is a flowchart illustrating a fabrication process for the construction of a lead as described in conjunction with FIGS. 5-7.

FIG. 10 is a flowchart illustrating a fabrication process for the construction of a lead as described in conjunction with FIGS. 5-7. In one embodiment, a lead sub-assembly 250 may be provided in a preassembled state to include a conductive element 112a, an internal jacket 130 surrounding the conductive element 112a, and an external jacket 140 extending about the internal jacket 130 [block 600]. In exemplary embodiments, the lead sub-assembly 250 may be prefabricated and procured on bulk spools. The appropriate length of prefabricated lead sub-assembly 250 is first cut from a bulk spool of material [block 605]. Electrode and/or connector termination locations are prepared at the appropriate locations of the lead sub-assembly 250 according to the type of lead and electrode configuration to be assembled [block 610]. For example, laser ablation may be used to remove the various layers of the external jacket 140 and internal jacket 130 covering the conductive element 112a. In alternate embodiments, a conductive fitting 320 may be coupled to the conductive element 112a during pre-fabrication of lead sub-assembly 250 in which case removal of the insulative jackets 130, 140 exposes the fitting 320; or, the conductive fitting 320 is coupled after removal of the insulative jackets 130, 140 [block 615]. Exemplary techniques such as crimping, welding, brazing, soldering or electrically conductive epoxy may be used to join the conductive fitting 320 to the conductive element 112a.

An electrode 350 is positioned adjacent to the appropriate electrode termination location (either on the conductive element 112a for direct coupling, or on the conductive fitting 320) [block 620]. Optionally, portions of the electrode 350 and conductive element 112a (or conductive fitting 320, as appropriate) may be placed under compression to prevent movement prior to completion of the coupling [block 625]. The material of the conductive element 112a (or conductive fitting 320, as appropriate) is then reflowed to cause a coating of the material to cover the electrode 350 [block 630]. The reflow may include heating the material of the conductive element 112a to a temperature that causes the material to melt. Examples of techniques to heat the material may include laser welding and any other techniques that can be employed to focus an energy source primarily on the conductive element 112a. Once the material of the conductive element 112a reaches a molten state, the material is manipulated to provide a coating on a portion of the electrode 350. Subsequently, the assembly comprising the electrode 350 and the coating or layer of material of the conductive element 112a is permitted to settle and fuse together [block 635]. According to one method of the present disclosure, the assembly may be cooled back to a room temperature.

In alternate embodiments, the external jacket 140 is placed subsequent to the construction of the fused assembly; alternatively, any additional components that could not be installed, for example, o-ring seals, steroid plugs, suture sleeves, etc., may then be installed [block 640].

As those skilled in the art will appreciate, the above discussion can be implemented in conjunction with new or known techniques of manufacturing medical electrical leads. For example, the lead sub-assembly 250 may be provided as a pre-assembled helical sub-assembly further including a removable core wire (not shown) contained as a build mandrel or build wire. The core wire may provide support to the lead sub-assembly 250 during handling in manufacturing. More importantly, the core wire may be pulled tightly in assembly jigs and fixtures, providing stable, straight, and precisely positionable helical lead sub-assemblies required for modular automated manufacturing processes. The core wire is easily withdrawn from the lead body or, more specifically, the helical lead sub-assembly 250, whenever required.

In some embodiments, the above-described method of manufacture is highly advantageous at least in part due to the structural integrity of the resulting conductive element 112a-to-electrode 350 junction. Prototype lead bodies built employing the construction techniques disclosed herein were tested and proven to have superior flex fatigue and tensile strength properties in addition to maintaining the required structural integrity, as compared to leads built with conventional techniques that were found to even exhibit multiple cracks.

Figure 11A:
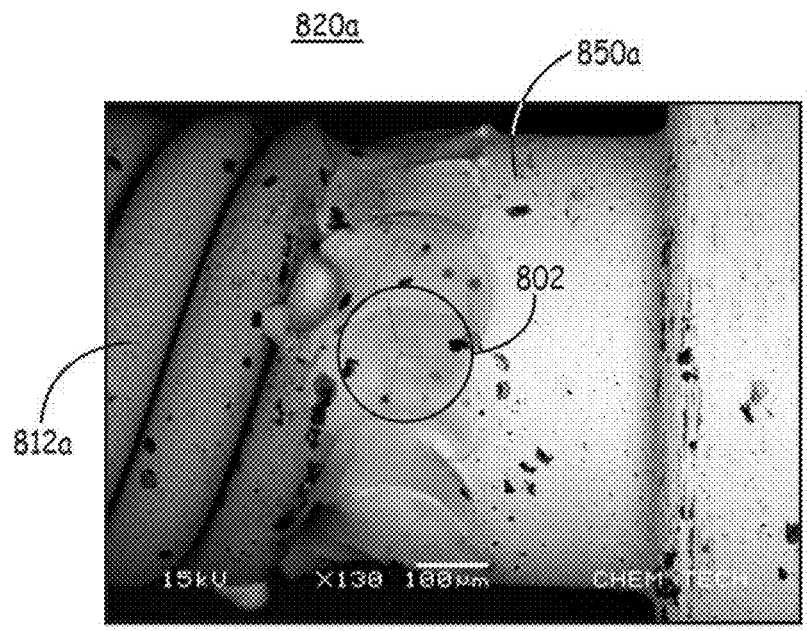
FIGS. 11A-C are scanning electron micrograph photographs of portions of two prototype lead bodies.
Figure 11B:
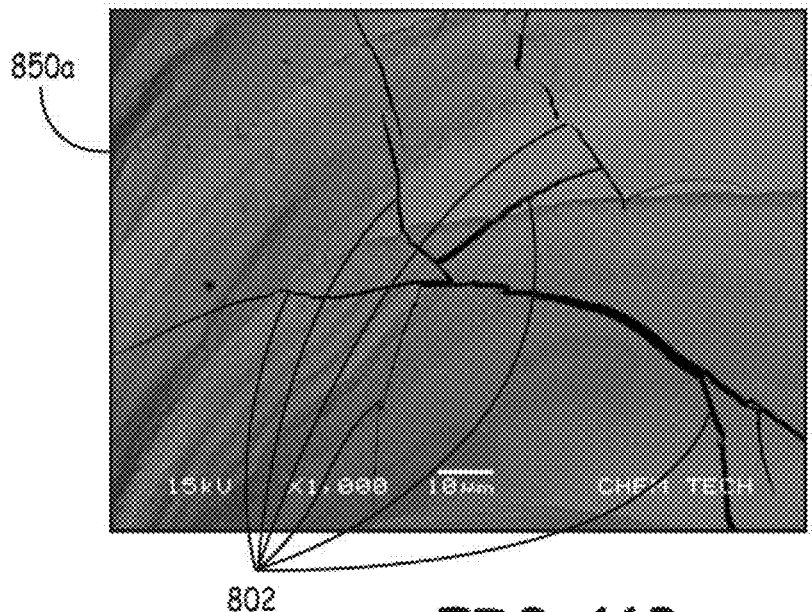
Figure 11C:
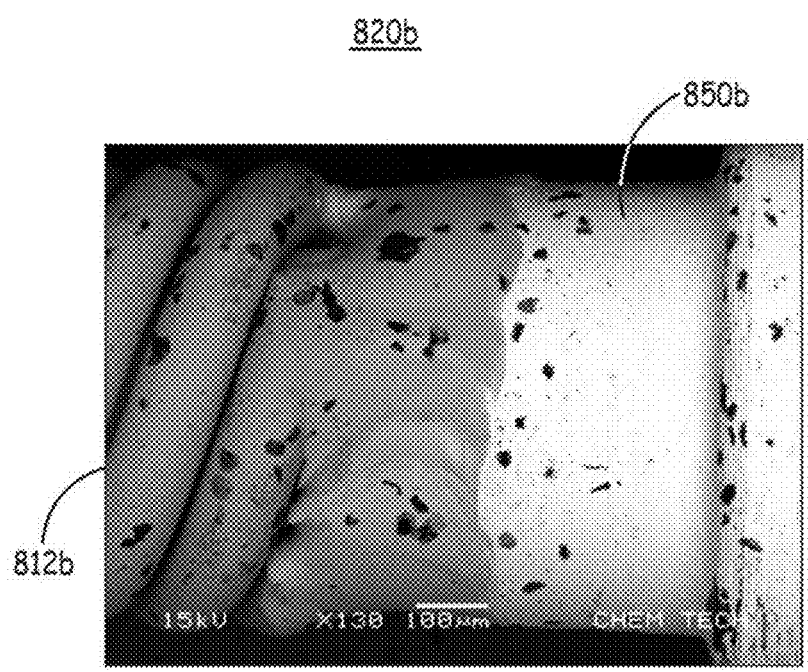

FIGS. 11A-C are scanning electron micrograph photographs of portions of two prototype lead bodies. The illustrative FIGS. 11A-D depict the outer surface of the junction between conductive elements 812a, 812b and electrodes 850a, 850b. Both leads were constructed from the same material; the material used for construction of conductive coils 812a, 812b was comprised of a cobalt alloy, MP35N having chemical structure 35Ni-35Co-20Cr-10Mo, whereas the material used for construction of the electrodes 850a, 850b was a tantalum alloy, with the chemical structure Ta-10Nb-6W. The prototype lead depicted in FIGS. 11A-B was constructed in accordance with conventional techniques whereas the prototype lead depicted in FIG. 11C was constructed in accordance with the exemplary techniques disclosed above.

Turning to FIG. 11A, the photograph shows a prototype lead 820a that exhibits cracks 802 resulting from the coupling, which in this test was utilized a conventional full fusion weld. FIG. 11B depicts an enlarged view of the cracks 802 formed on the prototype lead of FIG. 11A. As illustrated, the mechanical integrity of the prototype lead 820a is severely compromised by the cracks 802.

In contrast to the prototype lead 820a of FIG. 11A, the photograph in FIG. 11C depicts a prototype lead 820b that exhibited no visible deformation. FIG. 11C illustrates that the structural integrity of the resulting fused assembly was maintained. From these results, it is apparent that the construction techniques of the present disclosure provide a robust medical electrical lead with desirable structural integrity that offers superior flexibility and durability as compared to conventional construction techniques.

Although the present disclosure has been described with reference to preferred embodiments, persons skilled in the art will recognize that changes may be made in form and detail without departing from the spirit and scope of the disclosure. For example, although the disclosure generally relates to leads in which the conductors are coupled to electrodes, it should be understood that the construction techniques of the present disclosure are equally applicable to leads carrying other types of sensors, such as pressure sensors, temperature sensors and the like, as well as being applicable to leads which carry other types of electrically powered devices.

What is claimed is:

1. A method for manufacturing an implantable medical electrical lead device, comprising:
   providing a lead sub-assembly comprising an elongate conductor, an electrode and a first insulative layer, wherein the elongate conductor has a first thermal melting point and the electrode has a second thermal melting point that is higher than the first thermal melting point;
   covering at least a portion of the elongate conductor with the first insulative layer to form an elongate device body;
   positioning the electrode at a predetermined location on the elongate conductor; and
   coupling the electrode to the elongate conductor, wherein:
   the coupling includes reflowing the material of the elongate conductor onto the electrode and
   the reflowing comprises heating the lead sub-assembly to a temperature that causes the melting of the elongate conductor without melting the electrode.

2. The method of claim 1, further comprising:
   providing a conductive fitting; and
   coupling the conductive fitting to the elongate conductor at the predetermined location prior to positioning the electrode at the predetermined location, wherein the electrode is directly coupled to the conductive fitting.

3. The method of claim 1, further comprising:
   providing a second insulative layer; and
   covering the elongate device body with the second insulative body.

4. The method of claim 1, wherein the elongate conductor comprises a first material and the electrode comprises a second material.

5. The method of claim 4, wherein the first material consists essentially of at least one of the following: tantalum, platinum, gold, iridium, rhenium, tungsten, ruthenium, depleted uranium, cobalt, chromium, titanium, aluminum, vanadium, chromium, nickel, molybdenum, iron, copper, silver, gold, stainless steel, magnesium-nickel, palladium and alloys thereof.

6. The method of claim 4, wherein the first material consists essentially of a cobalt-based alloy.

7. The method of claim 4, wherein the second material consists essentially of at least one of the following: tantalum, platinum, gold, iridium, rhenium, tungsten, ruthenium, depleted uranium, cobalt, chromium, titanium, aluminum, vanadium, chromium, nickel, molybdenum, iron, copper, silver, gold, stainless steel, magnesium-nickel, palladium and alloys thereof.

8. The method of claim 4, wherein the second material consists essentially of tantalum.

9. The method of claim 1, further comprising providing an opening through the first insulative layer in proximity to the predetermined location prior to positioning the electrode.

10. The method of claim 9, wherein providing the opening comprises forming the opening by means of mechanical cutting.

11. The method of claim 9, wherein providing the opening comprises forming the opening by means of thermal cutting.

12. The method of claim 1, wherein coupling the electrode comprises melting the elongate conductor and manipulating the molten substance to cover a portion of the electrode.

13. The method of claim 1, wherein reflowing the exposed conductor is performed by resistance welding.

14. The method of claim 1, wherein reflowing comprises:
    melting a segment of the elongate conductor; and
    overlaying the molten segment of the elongate conductor over the portion of the electrode to create a mechanical contact between the elongate conductor and the electrode.

* * * * *